US00PP30706P2

(12) United States Plant Patent
Cain

(10) Patent No.: US PP30,706 P2
(45) Date of Patent: Jul. 16, 2019

(54) GRAPEVINE 'IFG THIRTY-FIVE'

(50) Latin Name: *Vitis vinifera*
Varietal Denomination: IFG Thirty-five

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/932,402

(22) Filed: Feb. 26, 2018

(51) Int. Cl.
*A01H 5/08* (2018.01)
*A01H 6/88* (2018.01)

(52) U.S. Cl.
USPC ..... Plt./207
CPC ..... *A01H 6/88* (2018.05)

(58) Field of Classification Search
USPC ..... Plt./207
See application file for complete search history.

*Primary Examiner* — Anne Marie Grunberg

(57) ABSTRACT

This invention is a new and distinct grapevine variety denominated 'IFG Thirty-five'. The new grapevine is characterized by producing naturally large size elliptic seedless berries having a strong muscat flavor, very thin skin and which ripens in mid-season. Berries are borne on medium size clusters which may require low rates of gibberellin to thin.

1 Drawing Sheet

Latin name of the genus and species claimed: *Vitis vinifera.*

Variety denomination: 'IFG Thirty-five'.

BACKGROUND OF THE INVENTION

The new and distinct grapevine described and claimed herein originated from a hand pollinated cross of the IFG 04125-018-209, an unnamed seedless selection from the IFG breeding program and IFG 05093-081-118, an unnamed seedless selection from the IFG breeding program hybridized in May 2009. The abortive seed traces were subsequently embryo cultured and the resulting 458 plants were planted in the field in April 2010. The present variety of grapevine was selected as a single plant in August 2011 and was first asexually propagated by hardwood cuttings in December 2011 near Delano, Kern County, Calif. The resulting propagules were planted during April 2012 near Delano, Kern County, Calif. and were found to reproduce true-to-type through at least two generations of asexual reproduction using hardwood cuttings.

BRIEF SUMMARY OF THE INVENTION

The new grapevine 'IFG Thirty-five' is characterized by producing naturally large size elliptic seedless berries having a strong muscat flavor, very thin skin and which ripens in mid-season. Berries are borne on medium size clusters which may require low rates of gibberellin to thin. Berries are highly responsive to Gibberellic acid applications to increase berry size. To the inventor's knowledge, the known variety to which the new grapevine variety is most similar is the Italia variety (unpatented). 'IFG Thirty-five' differs from the 'Italia' (non-patented) by being seedless rather than seeded, ripening approximately ten days earlier, having a thinner skin, having a more elliptic shape and more uniform berry size. 'IFG thirty-five' differs from its maternal parent, the IFG 04125-018-209 by producing larger more elliptic berries as opposed to the smaller more oval berries of IFG 04125-018-209. 'IFG Thirty-five' also has a stronger, more pronounced muscat flavor and has less tendency to bruise and brown than IFG 04125-018-209. It differs from its pollen parent, the IFG 05093-081-118, by producing larger more elliptic berries as opposed to the smaller more oval berries of IFG 05093-081-118, by being more uniform in berry size, and having less tendency to bruise and brown than IFG 05093-081-118.

BRIEF DESCRIPTION OF THE FIGURE

The accompanying photographic illustration illustrates in full color 'IFG Thirty-five'. The photograph was taken outdoors with indirect lighting. The colors are as nearly true as is reasonably possible in a color representation of this type.

The left side of the drawing has a mature leaf.

A mature fruit cluster and a typical berry in cross-section is represented in the center of the drawing.

A young shoot with tendrils can be seen on the right side of the drawing

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Thirty-five' plants grown in the vicinity of Delano, Kern County, Calif. during 2014 and 2015, and is believed to apply to plants of the variety grown under similar conditions of soil and climate elsewhere:

VINE

General:

*Vigor*.—Moderate.
*Density of foliage*.—Medium.
*Productivity*.—Medium, producing 23.6 to 35.4 kg of fruit per vine.
*Root stock*.—Own root.
*Training method*.—Typically spur pruned leaving 2 bud spurs.

Trunk:

*Trunk diameter of* 4-*year-old vines at* 30 *cm above the soil line*.—About 4.9 cm.
*Shape*.—Moderately slender.
*Strape*.—Short split.
*Surface texture*.—Smooth to slightly rough.
*Inner bark color*.—Greyed-orange: 165A.

SHOOTS

Young shoot:

*Form of tip*.—Wide open.
*Distribution of anthocyanin coloration of tip*.—Piping (striped).
*Intensity of anthocyanin coloration of tip*.—Weak.
*Density of prostrate hairs of tip*.—Sparse.
*Density of erect hairs of tip*.—Absent.
*Color*.—The following colors were observed: Yellow-green: N144A and occasionally Greyed-purple: 183A on some portions of shoots.

Woody shoot (mature canes):

*Shape*.—Stocky.
*Internode length*.—Long: About 11.9 cm.
*Width at node*.—About 1.6 cm.
*Cross section*.—Elliptic.
*Surface*.—Striate.
*Main color*.—The following colors were observed: Greyed-orange: 166A and 166B.
*Density of erect hairs of nodes*.—None or very sparse.
*Density of erect hairs on internodes*.—None or very sparse.
*Growth of axillary shoots*.—Weak: Approximately 1.2 cm.

Flowering shoot:

*Vigor during flowering*.—Moderate.
*Attitude during flowering on shoots not tied*.—Erect.
*Color*.—Dorsal side of internodes — Yellow-green: 146C, with Red-purple stripes: 59B.
*Color*.—Ventral side of internodes — Yellow-green: 146C.
*Color*.—Dorsal side of nodes — Yellow-green: 146C, with Red-purple stripes: 59B.
*Color*.—Ventral side of nodes — Yellow-green: 146C, with Red-purple stripes: 59B.
*Density of prostrate hairs of nodes*.—Very sparse.
*Density of erect hairs of nodes*.—None.
*Density of prostrate hairs on internode*.—Very sparse.
*Density of erect hairs on internode*.—None.
*Anthocyanin coloration of buds*.—Present.

Tendrils:

*Distribution on the shoot* (*at full flowering*).—Discontinuous.
*Length of tendril*.—Long: About 27.4 cm.
*Thickness of tendril* 2 *cm from base*.—About 2.5 mm.
*Color*.—The following colors were observed: Yellow-green: N144A and Greyed-purple: 183C at the tip of the tendrils.
*Form*.—Bifurcated.
*Number of consecutive tendrils*.—2.

LEAVES

Young leaves:

*Color of upper surface of first four distal unfolded leaves*.—Yellow-green: N144A.
*Average intensity of anthocyanin coloration of six distal leaves prior to flowering*.—Absent or very weak.
*Density of prostrate hairs between veins* (*lower surface*).—Very sparse.
*Density of prostrate hairs on veins* (*lower surface*).—Sparse.
*Density of erect hairs between veins* (*lower surface*).—Absent.
*Density of erect hairs on veins* (*lower surface*).—Very sparse.

Mature leaves:

*Average length*.—About 10.9 cm.
*Average width*.—About 17.9 cm.
*Mature leaf size*.—Medium.
*Shape of blade*.—Pentagonal.
*Number of lobes*.—5.
*Blade venation*.—Palmate.
*Anthocyanin coloration of main veins on upper side of blade*.—Absent.
*Mature leaf profile*.—Undulate.
*Blistering surface of blade upper surface*.—Absent.
*Leaf blade tip*.—In the plane of the leaf.
*Undulation of margin*.—Slight.
*Thickness*.—Medium.
*Undulation of blade between main and lateral veins*.—Absent.
*Shape of teeth*.—Both sides concave.
*Length of teeth*.—Medium.
*Ratio length/width of teeth*.—Small.
*Shape of upper lateral sinuses*.—Open to closed.
*Depth of upper lateral sinuses*.—Medium to deep.
*General shape petiole sinus*.—Wide open.
*Shape of base of upper leaf sinuses*.—V-shaped.
*Tooth at petiole sinus*.—Absent.
*Density of prostrate hairs between veins on lower surface of blade*.—Absent to very sparse.
*Density of erect hairs between veins on lower surface of blade*.—Absent.
*Density of prostrate hairs on main veins on lower surface of blade*.—Very sparse.
*Density of erect hairs on main veins on lower surface of blade*.—Very sparse.
*Density of prostrate hairs on main veins on upper surface of blade*.—Very sparse.
*Density of erect hairs on main veins on upper surface of blade*.—Very sparse.

*Autumn coloration of leaves*.—Leaves can be a single color or combination of colors, in a mottled pattern or on the edges of the leaves: The following colors were observed: Greyed-yellow: 162A and 162B.

Upper surface:

*Color*.—Green: 137A.

*Anthocyanin coloration of main veins*.—Absent.

*Surface appearance*.—Glossy.

*Blistering surface of blade*.—Weak.

Lower surface:

*Color*.—Yellow-green: 146B.

*Anthocyanin coloration of main veins* (*lower surface*).—Absent.

*Glossiness*.—Medium.

*Surface texture*.—Smooth.

*Surface appearance*.—Semi-glossy.

Petiole:

*Length*.—About 10.9 cm.

*Diameter of petiole* 2 *cm from blade*.—About 4.1 mm.

*Petiole color*.—The following colors were observed: Yellow-green: 145A and 145B.

*Length of petiole compared to middle vein*.—Equal.

*Density of prostrate hairs on petiole*.—Sparse.

*Density of erect hairs on petiole*.—None.

Buds:

*Bud fruitfulness*.—Basal: Mostly fruitful.

*Position of first fruitful shoot on previous season cane*.—$1^{st}$ to $2^{nd}$ node.

*Dormant bud length*.—About 5.6 mm.

*Dormant bud width perpendicular to shoot*.—About 6.9 mm.

*Dormant bud color*.—Greyed-orange: 166A.

*Time of bud burst*.—Medium: Mar. 6, 2015.

FLOWERS

General:

*Flower sex*.—Hermaphrodite.

*Length of first inflorescence*.—Short: About 12.4 cm long by 9.8 cm wide.

*Position of first flowering and fruiting node*.—$4^{th}$ node (current season growth).

*Number of inflorescence per flowering shoot*.—1.1 to 2: About 1.3.

*Time of bloom*.—Early as compared with similar varieties in the growing area of Delano, Calif.

*Date of full bloom*.—Apr. 3, 2015.

FRUIT

General:

*Ripening period*.—Mid-season: Approximately Aug. 10, 2015.

*Use*.—Fresh market.

*Keeping quality*.—Good.

*Resistance to*.—Insects: Average typical of *Vitis vinifera* species. Diseases: Average typical of *Vitis vinifera* species.

*Refractometer test*.—Soluble solids: Brix — About 18.8.

*Brix/acid*.—About 34.8%.

*Titratable acidity*.—About 0.54.

*Juice ph*.—About 3.81.

Cluster:

*Mature cluster length* (*peduncle excluded*).—About 18.5 cm.

*Mature cluster width*.—About 16.6 cm.

*Mature cluster weight*.—About 787 g.

*Bunch density*.—Medium.

*Number of berries*.—About 146.

*Form*.—Conical.

Peduncle:

*Lignification of peduncle*.—Medium.

*Length of peduncle*.—Medium to short. Approximately 3.4 cm.

Berry:

*Uniformity of size*.—Uniform.

*Single berry weight*.—About 6.6 g natural: to about 8.1 g when treated with gibberellic acid.

*Shape*.—Elliptic.

*Seeds*.—Absent.

*Cross section*.—Circular.

*Berry dimensions*.—Longitudinal axis: About 28.4 cm. Horizontal axis: About 19.9 cm.

*Berry firmness*.—Medium.

*Particular flavor*.—Muscat.

*Bloom* (*cuticular wax*).—Weak.

*Berry separation from pedicel*.—Medium.

*Skin color* (*without bloom*).—Yellow-green: 145A.

*Flesh color*.—Green-white 157A.

Skin:

*Thickness*.—Thin.

*Skin toughness*.—Tender.

*Reticulation*.—Absent.

*Tenacity*.—Tenacious to flesh.

What is claimed:

1. A new and distinct variety of grapevine as herein illustrated and described.

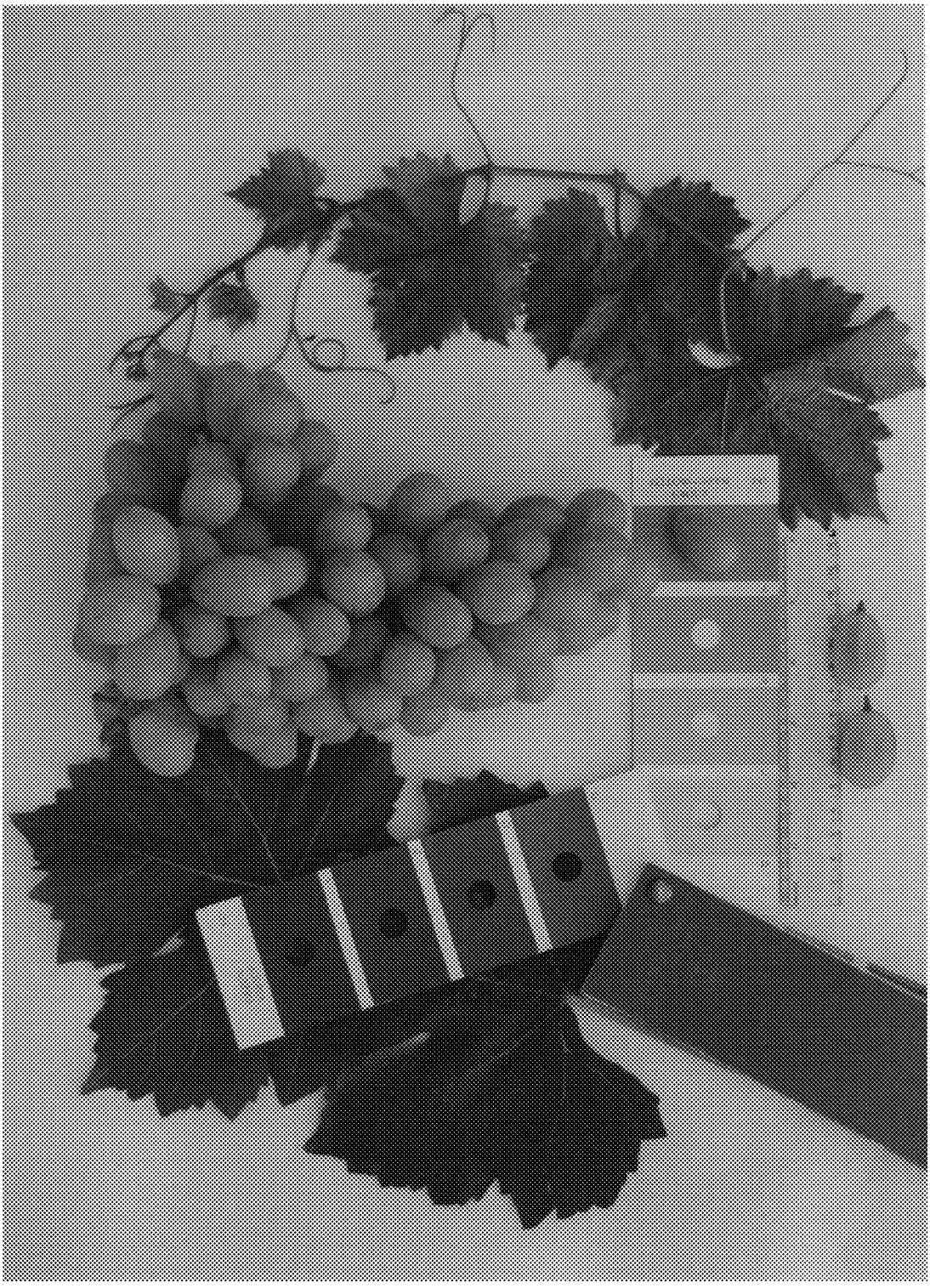

* * * * *